(12) United States Patent
Andersen

(10) Patent No.: US 8,863,756 B2
(45) Date of Patent: Oct. 21, 2014

(54) TOBACCO CHEWING GUM FORMULATION

(75) Inventor: Carsten Andersen, Vejle (DK)

(73) Assignee: Okono A/S (DK)

( * ) Notice: Subject to any disclaimer, the term of this patent is extended or adjusted under 35 U.S.C. 154(b) by 0 days.

(21) Appl. No.: 13/446,776

(22) Filed: Apr. 13, 2012

(65) Prior Publication Data

US 2012/0318287 A1    Dec. 20, 2012

Related U.S. Application Data

(60) Provisional application No. 61/499,041, filed on Jun. 20, 2011.

(51) Int. Cl.
| | | |
|---|---|---|
| *A24B 15/00* | (2006.01) | |
| *A61K 9/68* | (2006.01) | |
| *A24B 15/16* | (2006.01) | |
| *A61K 31/465* | (2006.01) | |
| *A23G 4/06* | (2006.01) | |

(52) U.S. Cl.
CPC ............... *A61K 9/0058* (2013.01); *A24B 15/16* (2013.01); *A61K 31/465* (2013.01); *A23G 4/068* (2013.01)
USPC ....................................................... 131/352

(58) Field of Classification Search
USPC ....................................................... 131/352
See application file for complete search history.

(56) References Cited

U.S. PATENT DOCUMENTS

| | | |
|---|---|---|
| 3,845,217 A | 10/1974 | Ferno et al. |
| 4,317,837 A | 3/1982 | Kehoe et al. |
| 4,545,392 A * | 10/1985 | Sensabaugh et al. ......... 131/352 |
| 5,488,962 A | 2/1996 | Perfetti |
| 2007/0062549 A1 * | 3/2007 | Holton et al. ................. 131/352 |

FOREIGN PATENT DOCUMENTS

| | | |
|---|---|---|
| EP | 1304048 A1 | 4/2003 |
| GB | 711187 A | 6/1954 |
| KR | 20010078976 A | 8/2001 |
| WO | 2009115160 A2 | 9/2009 |

OTHER PUBLICATIONS

English Translation of DE 202008005433, taken from EPONet website, on Jun. 14, 2013, http://worldwide.espacenet.com/publicationDetails/description?CC=EP&NR=2265263A2&KC=A2&FT=D&ND=5&date=20101229&DB=EPODOC&locale=en_EP.*

International Search Report and Written Opinion of the International Searching Authority; Application No. PCT/DK2012/000042; Issued: Jun. 8, 2012; Mailing Date: Jun. 20, 2012; 13 pages.

* cited by examiner

*Primary Examiner* — Richard Crispino
*Assistant Examiner* — Dionne Walls Mayes
(74) *Attorney, Agent, or Firm* — St. Onge Steward Johnston & Reens LLC

(57) ABSTRACT

A chewing gum formulation including tobacco particles and a gum base, where the gum base includes one or more hydrophobic gum base polymers, and where the tobacco particles are made from tobacco leaves. The amount of tobacco particles is between 0.5 and 30% by weight of the chewing gum formulation, and nicotine is released from the tobacco particles when chewing the chewing gum formulation.

23 Claims, No Drawings

TOBACCO CHEWING GUM FORMULATION

CROSS-REFERENCE TO RELATED APPLICATIONS

The present application claims the benefit, under 35 U.S.C. §119(e), of U.S. Provisional Patent Application No. 61/499,041 filed on Jun. 20, 2011, the content of which is incorporated herein by reference.

FIELD OF THE INVENTION

The present invention relates to the field of chewing gum. In particular the present invention relates to a tobacco chewing gum formulation.

BACKGROUND OF THE INVENTION

It is well known to use chewing gum comprising nicotine or complexes of nicotine to provide a user with appropriate doses of nicotine.

Considerable effort has been put into formulating chewing gum that can deliver nicotine to a user in a way close to what is experienced by a person when smoking a cigarette.

Different ways of incorporating the nicotine into the chewing gum by mixing or initial preparation of the nicotine have been disclosed in the prior art.

One of these prior art disclosures includes U.S. Pat. No. 5,488,962 specifically dealing with the problem of simulating the cigarette smoking with respect to the level of nicotine retention in the blood and saliva. According to the disclosure, an initial peak of nicotine level in the blood is obtained more similar to the corresponding absorption of nicotine when smoking a cigarette. The levels reached after a certain time corresponds to conventional nicotine-containing chewing gums.

A problem is, however, that the modification of the initial release may typically result in a relatively low release after only a few minutes.

It is an object of the present invention to obtain a nicotine release from chewing gum which, when compared to conventionally known nicotine-containing chewing gums, exhibits a faster release of nicotine both initially and within the first minutes of chewing; thereby providing a release of nicotine from the chewing gum closer to the release obtained when a user is smoking a cigarette.

SUMMARY OF THE INVENTION

The present invention relates to a chewing gum formulation comprising tobacco particles and a gum base, wherein the gum base comprises one or more hydrophobic gum base polymers, and wherein the tobacco particles are made from tobacco leaves,
  wherein the amount of tobacco particles is between 0.5 and 30% by weight of the chewing gum formulation,
  wherein nicotine is released from the tobacco particles when chewing the chewing gum formulation.

It has surprisingly been found by the present inventor that substantial and effective amounts of nicotine are released from a chewing gum formulation comprising tobacco particles. Impressive rates of nicotine release from a chewing gum formulation comprising tobacco particles may be achieved. As such this may be advantageous over conventional nicotine chewing gum when a fast release of nicotine is to be obtained.

In an embodiment of the invention, the tobacco particles comprise tobacco fibres and the tobacco fibres are retained in the gum base after a 10 minute chewing process.

It should be noted that tobacco fibres generally comprise a significant amount of cellulose fibres.

Accordingly, impressive rates of nicotine release are obtained and at the same time fibres of the tobacco particles are retained in the gum base. It may be a benefit that tobacco fibres are retained in the gum base, e.g. if the tobacco particles include harmful substances that may give rise to disorders in the human body. Especially, harmful substances that may give rise to disorders in the human body may in this way be encapsulated in the gum base and excluded to enter the human body.

Unless otherwise stated, when tobacco fibres or compounds are mentioned to be retained in the gum base or released from a chewing gum formulation after a chewing process this chewing process refers to the procedure set forth in the Ph. Eur. 6$^{th}$ ed. 2.9.25, at pH=7.4, a chewing rate of 60 chew per minute, and with the temperature of the medium at 37° C.

The measurement of the retained fibres or compounds may be established by measuring the amounts of retained tobacco fibres in the chewing gum after chewing or measuring the amounts of released tobacco fibres, whichever method is most appropriate.

The measurement of the retained fibres or compounds may be established by measuring the amounts remaining in the chewing gum after chewing or measuring the amounts of released components, whichever method is most appropriate.

Unless otherwise stated the retention of the tobacco particles in the gum base or the retention of the tobacco fibers from the tobacco in the gum base is measured as follows:

The chewing gum is chewed referring to the procedure set forth in the Ph. Eur. 6$^{th}$ ed. 2.9.25, at pH=7.4, a chewing rate of 60 chew per minute, and with the temperature of the medium at 37° C. for about 10 minutes.

The buffer is filtered through weighed filter paper and the residue on the filter paper is dried in an oven at about 50° C. until dry. After weighing the dried filter paper with residue and subtracting a blind (dried filter paper without residue), the result is taken as tobacco fibres from tobacco released from the chewing gum. This is then compared to the amount of tobacco fibres in the chewing gum before chewing. By subtracting the measured released amount form the amount originally present and dividing by the amount originally present, the percentage retained may be calculated.

In an embodiment of the invention chewing gum formulation comprises tobacco particles and a gum base, wherein the gum base comprises one or more hydrophobic gum base polymers, and wherein the tobacco particles are made from tobacco leaves,
  wherein the amount of tobacco particles is between 0.5 and 30% by weight of the chewing gum formulation,
  wherein nicotine is released from the tobacco particles when chewing the chewing gum formulation, and
  wherein at least 50% by weight, preferably at least 75% by weight of the tobacco particles have a size between 50 and 2000 µm, preferably between 100 and 1200 µm, such as between 300 and 750 µm.

According to an advantageous embodiment of the present invention the tobacco particles may be obtained by finely dividing tobacco leaves. To the surprise of the inventors a pleasant texture of the chewing gum may be obtained in this embodiment. In particular, it may be beneficial not to have too large particles in the chewing gum formulation. Such large particles may result in unpleasant chew characteristics. At the same time, a too large amount of very small dimensions may result in a too large release of nicotine. The preferred rate of the release of nicotine from the chewing gum may be found within the selected tobacco particle size range.

By the term "size" here is meant a measure of the maximum dimension of the tobacco particles.

In an embodiment of the invention a chewing gum formulation comprises tobacco particles and a gum base, wherein the gum base comprises one or more hydrophobic gum base polymers, and wherein the tobacco particles are made from tobacco leaves, wherein the amount of tobacco particles is between 0.5 and 30% by weight of the chewing gum formulation,
wherein nicotine is released from the tobacco particles when chewing the chewing gum formulation, and
wherein the tobacco particles have a water content ranging from 2 to 40% by weight, preferably 5 to 30% by weight, such as 10 to 20% by weight.

The presence of water in the tobacco particles may affect both the ease of handling the tobacco particles in the production and also the initial softness of the chewing gum formulation. In addition the release rate of nicotine may be improved by selection of a preferred range of water content of the tobacco particles.

It has surprisingly been found by the present inventor that a relatively broad range of water content in the applied tobacco particles gives rise to chewing gum formulations with superior quality both with respect to nicotine release, taste and texture compared to nicotine-containing chewing gum of the prior art.

In an embodiment of the invention a chewing gum formulation comprises tobacco particles and a gum base, wherein the gum base comprises one or more hydrophobic gum base polymers, and wherein the tobacco particles are made from tobacco leaves, wherein nicotine is released from the tobacco particles when chewing the chewing gum formulation, and
wherein the amount of tobacco particles is between 3-25%, such as 4-20%, or 5-15% by weight of the chewing gum formulation.

According to embodiments of the present invention, the amount of tobacco particles in the chewing gum formulation has a pronounced influence on the taste, texture and nicotine release.

In an embodiment of the invention a chewing gum formulation comprises tobacco particles and a gum base, wherein the gum base comprises one or more hydrophobic gum base polymers, and wherein the tobacco particles are made from tobacco leaves, wherein the amount of tobacco particles is between 0.5 and 30% by weight of the chewing gum formulation,
wherein nicotine is released from the tobacco particles when chewing the chewing gum formulation, and
wherein the amount of nicotine in the tobacco particles is between 0.2-10%, preferably 0.4-8%, such as 0.6-6% or 0.8-4% by weight of the tobacco particles.

The nicotine content of tobacco leaves may vary widely for different types of tobacco. According to advantageous embodiments of the present invention, the amount of nicotine in the tobacco particles may be higher than 0.2%. On the other hand, the amount of nicotine in the tobacco particles may, according to the aforementioned advantageous embodiments, be lower than 10% to better be able to mask the somewhat unpleasant taste of nicotine, when a certain amount of tobacco particles is applied.

In an embodiment of the invention a chewing gum formulation comprises tobacco particles and a gum base, wherein the gum base comprises one or more hydrophobic gum base polymers, and wherein the tobacco particles are made from tobacco leaves, wherein the amount of tobacco particles is between 0.5 and 30% by weight of the chewing gum formulation,
wherein nicotine is released from the tobacco particles when chewing the chewing gum formulation, and
wherein the content of nitrosamines in the tobacco particles is less than 5 mg TSNA (Tobacco specific nitrosamines)/kg tobacco, such as less than 2, less than 1 or less than 0.5 mg TSNA/kg tobacco.

Natural tobacco may contain carcinogenic nitrosamines, which have been shown to be harmful to man, mainly due to their carcinogenic properties. Therefore, when tobacco particles with a comparatively low content of nitrosamines are used in the chewing gum formulation, further advantageous embodiments of the present invention are obtained.

In an embodiment of the invention a chewing gum formulation comprises tobacco particles and a gum base, wherein the gum base comprises one or more hydrophobic gum base polymers, and wherein the tobacco particles are made from tobacco leaves, wherein the amount of tobacco particles is between 0.5 and 30% by weight of the chewing gum formulation,
wherein nicotine is released from the tobacco particles when chewing the chewing gum formulation, and
wherein the ratio by weight between gum base and tobacco particles is between 50:1 and 1:2, preferably between 25:1 and 1:1, such as between 10:1 and 2:1, and wherein the chewing gum formulation further comprises buffer.

The combination of tobacco particles and buffer in the chewing gum formulation has surprisingly shown synergistic effects with respect to both release of nicotine from the chewing gum formulation and the bio-availability of the released nicotine through the mucous membrane of the user.

In an embodiment of the invention a chewing gum formulation comprises tobacco particles and a gum base, wherein the gum base comprises one or more hydrophobic gum base polymers, and wherein the tobacco particles are made from tobacco leaves, wherein the amount of tobacco particles is between 0.5 and 30% by weight of the chewing gum formulation,
wherein nicotine is released from the tobacco particles when chewing the chewing gum formulation, and
wherein the tobacco fibres are retained in the gum base after a chewing process.

To the surprise of the inventor nicotine was seen to be released from the tobacco particles in the chewing gum formulation while the tobacco fibres surprisingly were retained in the gum base of the chewing gum formulation after chewing the formulation. In this way, the weight of the individual tobacco particle may diminish during the chewing process due to released substances, but a substantial part of the individual tobacco particle is retained in the gum base. In particular the tobacco fibre content of the tobacco particles may be retained in the chewing gum after a chewing process.

It has been found that the amount of gum base in the chewing gum influences the retention of tobacco particles or the retention of tobacco fibre content of the tobacco particles in the chewing gum formulation. A higher gum base content gives rise to a better retention which means that more tobacco fibres are retained in the chewing gum after chewing according to the procedures outlined above. When the gum base content of the chewing gum is lowered, the amount of retained tobacco fibres is less than for a higher gum base content.

In an embodiment of the invention a chewing gum formulation comprises tobacco particles and a gum base, wherein the gum base comprises one or more hydrophobic gum base polymers, and wherein the tobacco particles are made from tobacco leaves,
  wherein the amount of tobacco particles is between 0.5 and 30% by weight of the chewing gum formulation,
  wherein nicotine is released from the tobacco particles when chewing the chewing gum formulation, and
  wherein more than 0.5 mg nicotine, such as more than 0.8 mg or more than 1.0 mg, is released from the chewing gum formulation within the first 5 minutes from initiation of a chewing process.

It has surprisingly been found by the present inventor that if a relatively fast release of nicotine from the chewing gum formulation is to be obtained, according to the present invention, it is advantageous to use tobacco particles as the source of nicotine.

In an embodiment of the invention a chewing gum formulation comprises tobacco particles and a gum base, wherein the gum base comprises one or more hydrophobic gum base polymers, and wherein the tobacco particles are made from tobacco leaves,
  wherein the amount of tobacco particles is between 0.5 and 30% by weight of the chewing gum formulation,
  wherein nicotine is released from the tobacco particles when chewing the chewing gum formulation, and
  wherein the tobacco particles have been mixed into the gum base.

By mixing tobacco particles with the hydrophobic gum base polymers prior to mixing with other chewing gum ingredients, a moderated release of nicotine from the chewing gum formulation may be obtained. In the present context it was seen as a surprise by the inventors that it was possible to mix the tobacco particles with the hydrophobic gum base polymers. In particular it was not foreseen that it was possible to mix the tobacco particles with the hydrophobic gum base polymers, when tobacco particles with a content of water were applied.

In an embodiment of the invention a chewing gum formulation comprises tobacco particles and a gum base, wherein the gum base comprises one or more hydrophobic gum base polymers, and wherein the tobacco particles are made from tobacco leaves,
  wherein the amount of tobacco particles is between 0.5 and 30% by weight of the chewing gum formulation,
  wherein nicotine is released from the tobacco particles when chewing the chewing gum formulation, and
  wherein the tobacco leaves have been exposed to a heat steaming process, thereby reducing the viable bacterial and fungal numbers of the tobacco leaves by at least 80%, preferably at least 90%, such as 99 or 99.9.

Reducing the vial bacterial and fungal numbers in the tobacco leaves may lengthen the shelf life of the chewing gum formulation according to embodiments of the present invention. It has surprisingly been found by the present inventor that tobacco particles from tobacco leaves treated with different techniques to reduce the vial bacterial and fungal numbers can be used according to a preferred embodiment of the present invention. According to this embodiment, such treatments do not negatively affect the taste or release profile of the resulting chewing gum. In particular, a heat steaming process is advantageous.

In embodiments of the present invention, at least 50% by weight, preferably at least 75% by weight of the tobacco particles have a size between 50 and 2000 µm, preferably between 100 and 1200 µm, such as between 300 and 750 µm.

In embodiments of the present invention, at least 50% by weight, preferably at least 75% by weight of the tobacco particles have a size above 300 µm.

In embodiments of the present invention, at least 50% by weight, preferably at least 75% by weight of the tobacco particles have a size below 700 µm.

In embodiments of the present invention, the tobacco particles have been prepared such that less than 25% by weight, preferably less than 15% by weight of the tobacco particles is capable of passing through a 50 mesh screen.

In embodiments of the present invention, the tobacco particles have a water content ranging from 2 to 40% by weight, preferably 5 to 30% by weight, such as 10 to 20% by weight.

In embodiments of the present invention, the amount of moisture contained in the tobacco particles is at least 2% by weight, such as at least 4%, at least 6%, or at least 8% by weight of the tobacco particles comprised in the chewing gum formulation.

In embodiments of the present invention, the amount of tobacco particles in the chewing gum formulation is between 2-25%, such as 3-22%, 4-20% or 5-15% by weight of the chewing gum formulation.

In embodiments of the present invention, the amount of tobacco particles in the chewing gum formulation is at least 10 mg, such as at least 20 mg, at least 30 mg or at least 40 mg.

In embodiments of the present invention, the amount of tobacco particles in the chewing gum formulation is less than 400 mg, such as less than 300 mg, less than 200 mg or less than 120 mg.

In embodiments of the present invention, the amount of nicotine in the tobacco particles is between 0.2-10%, preferably 0.4-8%, such as 0.6-6% or 0.8-4% by weight of the tobacco particles.

In embodiments of the present invention, the amount of nicotine from the tobacco particles in the chewing gum formulation is between 0.5 and 10 mg, such as 1-8% or 1.5-6% by weight of the tobacco particles.

In embodiments of the present invention, the content of nitrosamines in the tobacco particles is less than 0.1 µg nitrosamines/mg nicotine, such as less than 0.05, less than 0.02 or less than 0.01 µg/mg nicotine.

In embodiments of the present invention, the content of nitrosamines in the tobacco particles is less than 5 µg nitrosamines/g tobacco, such as less than 2, less than 1, less than 0.5, less than 0.2 or less than 0.1 µg/g tobacco.

In embodiments of the present invention, the ratio by weight between gum base and tobacco particles is between 50:1 and 1:2, preferably between 25:1 and 1:1, such as between 10:1 and 2:1, and wherein the chewing gum formulation further comprises buffer.

In embodiments of the present invention, the amount of tobacco particles is between 0.5-10% by weight of the chewing gum formulation, wherein the amount of gum base is between 20 and 90% by weight of the chewing gum formulation and wherein the chewing gum formulation comprises a buffer.

In embodiments of the present invention, the amount of buffer is in the range of 0.1% to 10%, preferably 0.5% to 5% by weight of the chewing gum.

In embodiments of the present invention, the chewing gum formulation comprises buffer in an amount of less than 5%, such as less than 2%, less than 1%, or less than 0.5% by weight.

In embodiments of the present invention, the chewing gum formulation is substantially free of buffer.

In embodiments of the present invention, the buffer is selected from the group consisting of sodium carbonate, sodium hydrogen carbonate, potassium carbonate, potassium hydrogen carbonate, dipotassium phosphate, potassium citrate, or any combination thereof.

In embodiments of the present invention, the tobacco fibres are retained in the gum base after a chewing process.

In embodiments of the present invention, at least 20% by weight, at least 30% by weight, at least 40% by weight, 50% by weight, such as at least 60%, such as at least 65%, such as at least 70%, such as at least 75%, such as at least 80%, such as at least 85%, such as at least 90%, at least 95% or at least 99%, of the tobacco fibres are retained in the gum base about 10 minutes from initiation of a chewing process.

According to this embodiment of the invention, different mechanisms may apply. First of all, the weight of the individual tobacco particle may diminish during the chewing process due to released substances, but a substantial part of the individual tobacco particle is retained in the gum base. In this respect the meaning of "diminish" would refer to a weight reduction of the individual particle. Secondly, some individual tobacco particles or tobacco fibres may be released during the chewing process. A combination may also occur.

In embodiments of the present invention, the amount of tobacco particles in the chewing gum formulation is in the range of 20 mg to 400 mg, such as 30 mg to 300 mg or 40 mg to 120 mg,
  wherein, about 10 minutes from initiation of a chewing process, more than 0.8 mg nicotine, such as more than 1.1 mg or more than 1.5 mg, is released from the chewing gum formulation, and
  at the same time at least 20% by weight, at least 30% by weight, at least 40% by weight, at least 50% by weight, at least 60% by weight, such as at least 70%, at least 80%, at least 90%, at least 95% or at least 99%, of the tobacco fibres are retained in the gum base.

In embodiments of the present invention, more than 0.5 mg nicotine, such as more than 0.8 mg or more than 1.0 mg, is released from the chewing gum formulation within the first 5 minutes from initiation of a chewing process.

In embodiments of the present invention, more than 0.8 mg nicotine, such as more than 1.1 mg or more than 1.5 mg, is released from the chewing gum formulation within the first 10 minutes from initiation of a chewing process.

In embodiments of the present invention, more than 25% of the total nicotine content in the chewing gum formulation, such as more than 40% or more than 50%, is released from the chewing gum formulation within the first 5 minutes from initiation of a chewing process.

In embodiments of the present invention, more than 40% of the total nicotine content in the chewing gum formulation, such as more than 55% or more than 75%, is released from the chewing gum formulation within the first 10 minutes from initiation of a chewing process.

In embodiments of the present invention, the chewing process is carried out in vitro on a chewing machine in accordance with European Pharmacopeia 4 th. ed. 2.9.25, with a phosphate buffer with a pH of 7.4.

In embodiments of the present invention, the released amounts are measured when the chewing gum formulation is chewed in vitro in accordance with European Pharmacopeia 4th. ed. 2.9.25 in a pH 7.4 phosphate buffer.

In embodiments of the present invention, the tobacco particles have been mixed into the gum base.

In embodiments of the present invention, the tobacco particles are mixed into the chewing gum formulation along with the bulk portion of the chewing gum formulation.

In embodiments of the present invention, the gum base comprises elastomer in the range of 5-40% by weight of the gum base,
natural resin in the range of 8-45% by weight of the gum base, and
synthetic resin in the range of 5-50% by weight of the gum base.

In embodiments of the present invention, the chewing gum formulation comprises gum base in an amount of 15 to 95% by weight of the chewing gum formulation, preferably 20 to 90% by weight, such as 30 to 80% by weight, 40 to 75% by weight or 50 to 70% by weight.

In embodiments of the present invention, the chewing gum formulation comprises gum base in an amount of 100 mg to 5000 mg, preferably 200 mg to 3000 mg, more preferably 300 mg to 2000 mg, such as 500 mg to 1500 mg or 800 mg to 1200 mg.

In embodiments of the present invention, the chewing gum formulation comprises natural resins in an amount of 0.1 to 40%, preferably 1 to 30%, such as 3 to 25% or 5 to 20%, by weight of the chewing gum formulation.

In embodiments of the present invention, the chewing gum formulation comprises natural resins in an amount of at least 13% by weight of the chewing gum formulation.

In embodiments of the present invention, the chewing gum formulation comprises synthetic resins in an amount of 0.1 to 40%, preferably 1 to 30%, such as 3 to 25% or 5 to 20%, by weight of the chewing gum formulation.

In embodiments of the present invention, the chewing gum formulation comprises elastomer in an amount of at least 2% by weight of the chewing gum formulation, preferably at least 4% by weight of the chewing gum formulation.

In embodiments of the present invention, the chewing gum formulation comprises elastomer in an amount of less than 35% by weight of the chewing gum formulation, preferably less than about 25% by weight of the chewing gum formulation such as less than 20%, 15% or 10% by weight of the chewing gum formulation.

In embodiments of the present invention, the tobacco leaves have been exposed to a heat steaming process, thereby reducing the viable bacterial and fungal numbers of the tobacco leaves by at least 80%, preferably at least 90%, such as 99 or 99.9.

In embodiments of the present invention, the tobacco leaves have been exposed to a heat steaming process, thereby reducing the viable bacterial and fungal numbers in the tobacco leaves down below 10,000 CFU/g (colony-forming units per gram), such as below 1,000 or below 100 CFU/g.

In embodiments of the present invention, more than 15% of the total flavour content in the chewing gum formulation, such as more than 25% or more than 40%, is released from the chewing gum formulation within the first 5 minutes from initiation of a chewing process.

In embodiments of the present invention, more than 20% of the total flavour content in the chewing gum formulation, such as more than 35%, more than 50% or more than 70%, is released from the chewing gum formulation within the first 10 minutes from initiation of a chewing process.

In embodiments of the present invention, the chewing gum formulation comprises one or more flavoring agents selected from the group consisting of essential oils, essences, extracts, powders, acids, coconut, coffee, chocolate, vanilla, grape fruit, orange, lime, menthol, liquorice, caramel aroma, honey aroma, peanut, walnut, cashew, hazelnut, almonds, pineapple, strawberry, raspberry, apple, pear, peach, apricot, blackberry, cherry, pineapple, plum essence, clove oil, bay oil, anise, thyme, cedar leaf oil, nutmeg, cinnamon, peppermint, wintergreen, spearmint, eucalyptus, mint, or any combination thereof.

In embodiments of the present invention, the chewing gum formulation comprises at least one of brightleaf, burley-leaf, oriental-leaf tobacco, Dark air cured Burley, Flue cured Virginia, and dark fired Kentucky.

In embodiments of the present invention, the chewing gum formulation comprises humectants, such as propylene glycol or glycerol.

In embodiments of the present invention, the chewing gum formulation comprises enhancers such as cocoa solids, licorice, tobacco extracts, and sugars.

In embodiments of the present invention, the chewing gum formulation is provided with a coating.

In embodiments of the present invention, the chewing gum formulation has a weight in the range of 0.1 to 10 grams, preferably in the range of 0.5 to 4 grams.

In embodiments of the present invention, the chewing gum comprises filler in an amount of 0.1 to 50% by weight of the chewing gum.

According to an advantageous embodiment of the invention, the chewing may comprise filler. The filler may advantageously be suitable for facilitating the water uptake of the fibres of the tobacco particles and it may also be suitable for facilitating the release of the ingredients of the tobacco particles when a user chews the chewing gum. In particular, it is noted that the filler may advantageously support the functionality of the fibres contained in the tobacco powder.

In embodiments of the present invention, the chewing gum comprises filler in an amount of 0.1 to 50% by weight of the chewing gum, wherein the filler is hydrophobic and wherein at least 90% of the filler is contained in the chewing gum throughout the chewing of a user during a chewing period of at least 10 minutes.

According to an advantageous embodiment of the invention the chewing gum comprises filler in an amount of 0.1 to 50% by weight of the chewing gum, wherein the filler is hydrophobic and wherein at least 90% of the filler is contained in the chewing gum throughout the chewing of a user during a chewing period of at least 10 minutes.

The chewing of the chewing gum throughout the period of at least 10 minutes may be set forth by the procedure set forth in the Ph. Eur. $6^{th}$ ed. 2.9.25, at pH=7.4, a chewing rate of 60 chew per minute, and with the temperature of the medium at 37° C., whereas the measurement of the retained filler may be established by measuring on the remaining chewing gum or measuring of the released components, whichever method is most appropriate.

In embodiments of the present invention, the chewing gum comprises filler in an amount of 0.1 to 50% by weight of the chewing gum and wherein the filler comprises magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood, and combinations thereof.

In embodiments of the present invention, the chewing gum is a compressed chewing gum tablet.

In embodiments of the present invention, the compressed chewing gum tablet is a multi-layer tablet.

In embodiments of the present invention, the chewing gum has the form of a slab or stick.

In an embodiment of the invention, the tobacco particles comprises tobacco fibres and at least 20% of the tobacco fibres are retained in the gum base after a 10 minute chewing process.

In embodiments of the present invention, at least 30%, preferably at least 40% and even more preferred at least 50% of the tobacco fibres are retained in the chewing gum after the chewing gum has been chewed in vitro in accordance with European Pharmacopeia 4th. ed. 2.9.25 in a pH 7.4 phosphate buffer for 10 minutes.

In embodiments of the present invention, at least 60% of the tobacco fibres are retained in the chewing gum after the chewing gum has been chewed in vitro in accordance with European Pharmacopeia 4th. ed. 2.9.25 in a pH 7.4 phosphate buffer for 10 minutes.

In embodiments of the present invention, at least 70% of the tobacco fibres are retained in the chewing gum after the chewing gum has been chewed in vitro in accordance with European Pharmacopeia 4th. ed. 2.9.25 in a pH 7.4 phosphate buffer for 10 minutes.

In embodiments of the present invention, at least 80% of the tobacco fibres are retained in the chewing gum after the chewing gum has been chewed in vitro in accordance with European Pharmacopeia 4th. ed. 2.9.25 in a pH 7.4 phosphate buffer for about 10 minutes.

In embodiments of the present invention, at least 85% of the tobacco fibres are retained in the chewing gum after the chewing gum has been chewed in vitro in accordance with European Pharmacopeia 4th. ed. 2.9.25 in a pH 7.4 phosphate buffer for about 10 minutes.

In an embodiment of the invention the relative release of nicotine from the tobacco powder in the chewing gum formulation is greater than the relative release of tobacco fibres from the chewing gum formulation when the chewing gum formulation is chewed for 10 minutes.

Moreover, the invention relates to a method of preparing a chewing gum formulation comprising tobacco particles and gum base, the method comprising the steps of:
preparing a gum base and
blending the gum base with tobacco particles, an effective amount of buffer and other chewing gum ingredients at a temperature below 60° C.

Moreover, the invention relates to a method of preparing a chewing gum formulation comprising tobacco particles and gum base,
wherein the tobacco particles is mixed with other chewing gum ingredients including the hydrophobic gum base constituents in the chewing gum formulation and an effective amount of buffer, the mixing being performed at a temperature below 60° C.

DETAILED DESCRIPTION OF THE INVENTION

By the terms "gum base" and "gum base matrix" we mean the mainly water insoluble and hydrophobic gum base ingredients that are mixed together before the bulk portion of the chewing gum formulation is added.

The term "bulk portion" intends to mean the mainly water soluble chewing and hydrophilic gum ingredients that are mixed into the gum base matrix after it has been mixed.

The term "weight of the chewing gum formulation" or similar wording meaning the same is defined in the present context as weight of the chewing gum formulation, without including the weight of an outer coating, such as a hard coating, soft coating, and the like.

By the phrase "chewing gum" is meant any chewing gum such as extruded chewing gum, centre-filled chewing gum, toffee-imitating chewing gum, compressed chewing gum, slabs or sticks.

By the phrase "texture" is meant a qualitative measure of the visco-elastic properties of the chewing gum and of the overall mouth-feel experienced by the user during the chewing process. Thus the term "texture" encompasses measurable quantities such as hardness and elasticity as well as more subjective parameters related to the chew-feel experienced by a user.

By the phrase "retained" is meant that e.g. fibres of tobacco powder are contained within the gum base of the chewing gum formulation after it has been chewed.

The phrase "hydrophobic" is used to describe the ability of a substance to dissolve in or blend with apolar substances such as e.g. oils.

The phrase hydrophilic is used to describe the ability of a substance to dissolve in or blend with polar substances, such as e.g. water.

By the phrase "tobacco particles" is meant small parts made from tobacco leaves by conventional techniques.

According to embodiments of the invention, the gum base matrix may constitute 50 to 80% by weight of the chewing gum formulation. The amount of gum base may in some embodiments constitute 60 to 70% by weight of the chewing gum formulation. According to other embodiments of the invention, the gum base matrix may constitute 20 to 50% by weight of the chewing gum formulation. The amount of gum base may in some embodiments constitute 30 to 40% by weight of the chewing gum formulation.

In some embodiments of the invention, a buffer is added, the buffer being selected from the group consisting of a tris buffers, amino acid buffers, carbonate, including monocarbonate, bicarbonate or sesquicarbonate, glycerinate, phosphate, glycerophosphate, acetate, glyconate or citrate of an alkali metal, such as potassium and sodium, e.g. trisodium and tripotassium citrate, or ammonium, and mixtures thereof.

When buffer is used, a preferred buffer is sodium bicarbonate. In some embodiments buffer is not part of the chewing gum formulation. In some other embodiments, buffer is part of the chewing gum formulation.

In some embodiments of the invention, the amount of buffer is 0.5 to 10% by weight of the chewing gum formulation.

In some embodiments of the invention the buffer is selected from the group consisting of a carbonate, including monocarbonate, bicarbonate or sesquicarbonate, glycerinate, phosphate, glycerophosphate, acetate, glyconate or citrate of an alkali metal, such as potassium and sodium, e.g. trisodium and tripotassium citrate, or ammonium, tris buffer, amino acids, and mixtures thereof.

In some embodiments of the invention the buffer is selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

The buffer may to some extent be microencapsulated or otherwise coated as granules with polymers and/or lipids being less soluble in saliva than is the one or more buffering agents. Such microencapsulation controls the dissolution rate whereby is extended the time frame of the buffering effect.

However, in a presently preferred embodiment an alkaline buffer is preferred, such as sodium carbonate.

According to the invention the presence of buffer allows in synergy with tobacco particles in the chewing gum formulation to adjust the release of nicotine from the tobacco particles and the bioavailability of the released nicotine in the oral cavity.

According to the invention a preferred amount of gum base matrix in the final chewing gum is above 30 percent by weight of the chewing gum core, such as above 35 percent by weight of the chewing gum core, such as above 40 percent by weight of the chewing gum core, such as above 45 percent by weight of the chewing gum core, such as about 40 percent by weight of the chewing gum core, such as about 47 percent by weight of the chewing gum core.

The formulation of gum base formulations can vary substantially depending on the particular product to be prepared and on the desired masticatory and other sensory characteristics of the final product. However, typical ranges (% by weight) of the above gum base components are: 5 to 80% by weight elastomeric compounds, 5 to 80% by weight elastomer plasticizers, 0 to 40% by weight of waxes, 5 to 35% by weight softener, 0 to 50% by weight filler, and 0 to 5% by weight of miscellaneous ingredients such as antioxidants, colourants, etc. The gum base may comprise about 5 to about 95 percent, by weight, of the chewing gum, more commonly the gum base comprises 10 to about 60 percent, by weight, of the gum.

Elastomers provide the rubbery, cohesive nature to the gum, which varies depending on this ingredient's chemical structure and how it may be compounded with other ingredients. Elastomers suitable for use in the gum base and gum of the present invention may include natural or synthetic types.

Elastomer plasticizers vary the firmness of the gum base. Their specificity on elastomer inter-molecular chain breaking (plasticizing) along with their varying softening points cause varying degrees of finished gum firmness and compatibility when used in base. This may be important when one wants to provide more elastomeric chain exposure to the alkane chains of the waxes.

The elastomers (rubbers) employed in the gum base may vary depending upon various factors such as the type of gum base desired, the texture of gum formulation desired and the other components used in the formulation to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum base formulations include, without limitation, natural substances (of vegetable origin) such as chicle gum, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

In some embodiments of the present invention tobacco powder is added to the gum base together with other gum base ingredients.

Natural resins may be used according to the invention and may be natural rosin esters, often referred to as ester gums including as examples glycerol esters of partially hydrogenated rosins, glycerol esters of polymerised rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

In an embodiment of the invention, the resin comprises terpene resins, e.g. derived from alpha-pinene, beta-pinene, and/or d-limonene, natural terpene resins, glycerol esters of gum rosins, tall oil rosins, wood rosins or other derivatives thereof such as glycerol esters of partially hydrogenated rosins, glycerol esters of polymerized rosins, glycerol esters of partially dimerised rosins, pentaerythritol esters of partially hydrogenated rosins, methyl esters of rosins, partially hydrogenated methyl esters of rosins or pentaerythritol esters of rosins and combinations thereof.

In an embodiment of the invention, said chewing gum ingredients are selected from the group consisting of bulk sweeteners, flavors, dry-binders, tabletting aids, anti-caking agents, emulsifiers, antioxidants, enhancers, absorption enhancers, buffers, high intensity sweeteners, softeners, colors, or any combination thereof.

The tobacco particles may in some embodiments of the invention be added to the chewing gum as a part of the bulk portion together with the other chewing gum ingredients.

In an embodiment of the invention, the chewing gum formulation comprises sweeteners, such as bulk sweeteners, sugar sweeteners, sugar substitute sweeteners, artificial sweeteners, high-intensity sweeteners, or any combination thereof.

Suitable bulk sweeteners include both sugar and non-sugar sweetening components. Bulk sweeteners typically constitute from about 5 to about 95% by weight of the chewing gum, more typically about 20 to about 80% by weight such as 30 to 70% or 30 to 60% by weight of the gum.

Useful sugar sweeteners are saccharide-containing components commonly known in the chewing gum art including, but not limited to, sucrose, dextrose, maltose, dextrins, trehalose, D-tagatose, dried invert sugar, fructose, levulose, galactose, corn syrup solids, and the like, alone or in combination.

Sorbitol can be used as a non-sugar sweetener. Other useful non-sugar sweeteners include, but are not limited to, other sugar alcohols such as mannitol, xylitol, hydrogenated starch hydrolysates, maltitol, isomalt, erythritol, lactitol and the like, alone or in combination.

High intensity artificial sweetening agents can also be used alone or in combination with the above sweeteners. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, sterioside and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another chewing gum component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the chewing gum formulation.

A chewing gum base formulation may, if desired, include one or more fillers/texturisers including as examples, magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood, and combinations thereof.

A number of chewing gum components well known within the art may be applied within the scope of the present invention. Such components comprise but are not limited to waxes, fats, softeners, fillers, flavors, anti-oxidants, emulsifiers, colouring agents, binding agents and acidulants In an embodiment of the invention, the chewing gum formulation is provided with an outer coating.

In an embodiment of the invention, said outer coating is selected from the group consisting of hard coating, soft coating and edible film-coating or any combination thereof.

The following non-limiting examples illustrate different variations of the present invention. The examples are meant for indicating the inventive concept; hence the mentioned examples should not be understood as exhaustive for the present invention.

EXAMPLES

Example 1

Preparation of Gum Base without Tobacco Particles

The composition of a gum base is presented in Table 1.

TABLE 1

| Gum base composition. Amounts are given in wt-% of the gum base. | |
|---|---|
| | GB std. |
| Elastomer | 16.0 |
| Resins | 44.5 |
| Filler | 15.0 |
| Plasticizers | 24.4 |
| Antioxidant | 0.1 |

GB = Gum Base.

The preparation of gum base is carried out by first adding a high-molecular weight elastomer, synthetic resin and filler to a heated (about 120° C.) and running z-blade mixer. After about twenty minutes of mixing, natural resin is added to the running mixer and mixing is continued for about five minutes followed by addition of further natural resin. After about five minutes of continued mixing, some plasticizer and further elastomer are added to the running mixer, and mixing is continued for about five minutes before addition of further plasticizer and antioxidant to the running mixer. Mixing is continued for about half an hour to one hour, and the final gum base mass is emptied from the mixer into coated or lined pans, extruded or cast into any desirable shape. Those skilled in the art will recognize that many variations of the above-described procedure may be followed.

Example 2

Preparation of Chewing Gum

In the present example, the gum base standard from example 1 GB std. was made into chewing gum CG std. with the composition as described in Table 2.

TABLE 2

Amounts are given in % by weight of the chewing gum formulation.

|  | CG std. |
|---|---|
| GB std. | 42 |
| Tobacco particles | 5 |
| Bulk Sweetener Sorbitol | 50.3 |
| Tobacco flavour | 2 |
| Intense sweeteners | 0.7 |

CG = Chewing Gum

A conventional mechanical mixing procedure is used. The gum base is added to a mixing kettle provided with mixing means like e.g. horizontally placed Z-shaped arms. The kettle had been preheated to a temperature of up to approximately 50° C., and the other ingredients are added according to a specified time schedule. Obviously, the amount of ingredients used may be varied within the scope of the present invention.

The chewing gum formulation may optionally be coated by means of hard coating. The coating may e.g. be applied according to conventional coating methods. The pieces evaluated are without coating.

Example 3

Preparation of Chewing Gum with Tobacco Particles, Size/Amount

Chewing gums comprising varying sizes and amounts of tobacco particles were made according to various embodiments of the present invention.

The chewing gum of example 2 was used with tobacco particles with tobacco amount and size as indicated in Table 3 replacing the corresponding amount of bulk sweetener. The resulting chewing gums are in Table 3 named for later reference.

TABLE 3

Avg. size is the average maximum dimension of the tobacco particles and the amount of tobacco is given in % by weight of the chewing gum

| | Avg. size (μm) | | | | |
|---|---|---|---|---|---|
| Tobacco (wt-%) | 40 | 250 | 500 | 750 | 2500 |
| 1 | CG01 | CG06 | CG11 | CG16 | CG21 |
| 5 | CG02 | CG07 | CG12 | CG17 | CG22 |
| 10 | CG03 | CG08 | CG13 | CG18 | CG23 |
| 20 | CG04 | CG09 | CG14 | CG19 | CG24 |
| 30 | CG05 | CG10 | CG15 | CG20 | CG25 |

The chewing gum with lower tobacco content (1-5 wt-%) had a mild taste of tobacco while with higher tobacco content (10-30 wt-%) had a distinct and pleasant tobacco taste.

Example 4

Preparation of Chewing Gum with Tobacco Particles, Nicotine Content

Chewing gums comprising tobacco particles with varying nicotine content were made according to various embodiments of the present invention. The varying nicotine content may be obtained by using either low- and/or high-nicotine containing types of tobacco in any combination. Hereby a desired nicotine content in the tobacco particles to be used may be obtained as seen in Table 4 below.

The chewing gum of example 2 was used with different types of tobacco particles replacing the corresponding amount of bulk sweetener, which contained amounts of nicotine as indicated in Table 4. The resulting chewing gums are in Table 4 named for later reference.

TABLE 4

The amount of tobacco is given in % by weight of the chewing gum and the amount of nicotine is given in % by weight of the tobacco.

| | Tobacco (wt-%) | | | | |
|---|---|---|---|---|---|
| Nicotine (wt-%) | 1 | 5 | 10 | 20 | 30 |
| 0.3 | CG26 | CG31 | CG36 | CG41 | CG46 |
| 0.7 | CG27 | CG32 | CG37 | CG42 | CG47 |
| 1.7 | CG28 | CG33 | CG38 | CG43 | CG48 |
| 3.4 | CG29 | CG34 | CG39 | CG44 | CG49 |
| 8.4 | CG30 | CG35 | CG40 | CG45 | CG50 |

Surprisingly, the chewing gums with highest nicotine content still had a pleasant taste and texture.

Example 5

Preparation of Chewing Gum with Tobacco Particles, Moisture Content

Chewing gums comprising tobacco particles with varying moisture content were made according to various embodiments of the present invention. The varying moisture content may be obtained by drying or adding extra water to any type of tobacco before adding it to the chewing gum. Hereby a desired moisture content in the tobacco particles to be used may be obtained as seen in Table 5 below.

The chewing gum of example 2 was used with tobacco particles, which had a moisture content as indicated in Table 5, replacing the corresponding amount of bulk sweetener. The resulting chewing gums are in Table 5 named for later reference.

TABLE 5

The amount of tobacco is given in % by weight of the chewing gum and the moisture content is given in % by weight of the tobacco.

| | Tobacco (wt-%) | | | | |
|---|---|---|---|---|---|
| Moisture (wt-%) | 1 | 5 | 10 | 20 | 30 |
| 2 | CG51 | CG56 | CG61 | CG66 | CG71 |
| 5 | CG52 | CG57 | CG62 | CG67 | CG72 |
| 11 | CG53 | CG58 | CG63 | CG68 | CG73 |
| 18 | CG54 | CG59 | CG64 | CG69 | CG74 |
| 26 | CG55 | CG60 | CG65 | CG70 | CG75 |

Surprisingly, the moisture content of the tobacco particles may be varied without compromising taste and texture of the chewing gum.

Example 6

Preparation of Chewing Gum with Tobacco Particles, Buffer

Chewing gums comprising tobacco particles with varying sizes were combined with various amounts of buffer according to various embodiments of the present invention.

The chewing gum of example 2 was used with buffer in amounts as indicated in Table 6 and tobacco particles in an amount of 5% of the chewing gum replacing the corresponding amount of bulk sweetener. The buffer used was a 50/50 by weight of NaHCO$_3$ and Na$_2$CO$_3$. The resulting chewing gums are in Table 5 named for later reference.

TABLE 6

The nicotine content is given in % by weight of the tobacco particles and the buffer content is given in % by weight of the chewing gum

| | Nicotine (wt-%) | | |
|---|---|---|---|
| Buffer (wt-%) | 0.7 | 2.4 | 4.3 |
| 0 | CG76 | CG81 | CG86 |
| 0.5 | CG77 | CG82 | CG87 |
| 3 | CG78 | CG83 | CG88 |
| 6 | CG79 | CG84 | CG89 |
| 8 | CG80 | CG85 | CG90 |

Example 7

Preparation of Chewing Gum with Tobacco Particles, GB-Ingredients

Chewing gums with tobacco particles in combination with varying gum base ingredients were made according to various embodiments of the present invention. The resulting gum bases were made into chewing gums in accordance with the description in example 2. The resulting chewing gums are in Table 7 named for later reference.

TABLE 7

The content of the individual ingredients are given in % by weight of the gum base.

| | CG91 | CG92 | CG93 | CG94 | CG95 | CG96 | CG97 |
|---|---|---|---|---|---|---|---|
| Elastomer | 16.0 | 17.5 | 10.0 | 16.0 | 13.0 | 19.0 | 15.0 |
| Resins | 44.5 | 48.0 | 49.7 | 40 | 37.5 | 26.5 | 32.5 |
| Filler | 1.0 | 2.5 | 2.6 | 6.5 | 11.0 | 16.0 | 4.0 |
| Plasticizers | 24.4 | 18 | 23.6 | 23.5 | 24.4 | 24.4 | 34.4 |
| Antioxidant | 0.1 | 0.05 | 0.1 | 0.0 | 0.1 | 0.1 | 0.1 |
| Tobacco | 14 | 14 | 14 | 14 | 14 | 14 | 14 |

Example 8

In Vitro Release of Nicotine

The release rate of nicotine from CG14 in Example 3 with tobacco particles with app. 11% moisture content and 2-3% nicotine, was measured according to the procedure set forth in the Ph. Eur. 6$^{th}$ ed. 2.9.25, at pH=7.4, a chewing rate of 60 chew per minute, and with the temperature of the medium at 37° C. With the same setting, the release rate from three prior art pieces, PA1, PA3, PA4, of nicotine gum was measured for comparison. The release rate can be seen in Table 8.

TABLE 8 the time given is from initiation of a chewing process as described and the values given are % by weight of the total content of nicotine in the products

| Time | CG14 (Wt-%) | PA4 (Wt-%) | CG98 (Wt-%) | PA1 (Wt-%) | PA3 (Wt-%) |
|---|---|---|---|---|---|
| 5 min | 61 | 51 | 83 | 45 | 15 |
| 10 min | 85 | 72 | 91 | 66 | 36 |
| 20 min | 89 | 92 | 95 | 83 | 56 |
| 30 min | 90 | 95 | 97 | 90 | 70 |

The results clearly show a significantly faster release of nicotine from the tobacco chewing gum formulation according to an embodiment of the present invention as compared to conventional nicotine gum.

A number of further measurements were carried out with other chewing gums with varying contents of tobacco particles, elastomers, resins and buffer were tested and showed in general an improved faster release of nicotine as compared to conventional chewing gum.

It is noted that the CG14 and PA4 are directly comparable and both have the same gum base composition and gum base content.

The gum base content and gum base composition is also the same for CG98 and PA1 but differs from CG14 and PA4.

The chewing gum composition of PA3 is unknown but refers to a Nicorette nicotine chewing gum where nicotine is contained in the form of a nicotine polacrilex resin (NPR), as is also the case for PA1 and PA4.

Example 9

In Vitro Release, Retention of Fibres of Tobacco Particles

The retention of the fibres of tobacco particles in the gum base upon chewing chewing gum was investigated by carrying out the procedure set forth in the Ph. Eur. 6$^{th}$ ed. 2.9.25, at pH=7.4, a chewing rate of 60 chew per minute, and with the temperature of the medium at 37° C.

The chewing time was 10 minutes.

The buffer from the chewing process was collected and filtered through weighed filter paper (pore size 5-10 micrometer) and dried in an oven at 50° C. until dry.

CG99 was a extruded chewing gum pellet comprising tobacco powder corresponding to a nicotine content of 2% by weight of the pellet.

CG100 was a 2 layer compressed chewing gum tablet with tobacco powder in one layer corresponding to a nicotine content of 2% by weight of the tablet.

CG102 was an extruded chewing gum pellet comprising no tobacco powder and thus represents a blind.

TABLE 9

Release of tobacco fibers from chewing gum tablets and chewing gum pellets compared to a blind.

| Product | Initial amount tobacco powder mg | Filter paper Mg | Dried filter paper with fibers mg | Fibers retained on the filter mg | Fibers retained on the filter corrected for blind mg | Release of fibers (>10 μm) from chewing gum % |
|---|---|---|---|---|---|---|
| CG99 | 127 | 547 | 558.4 | 11.4 | 17.8 | 35 |
| CG100 | 97.6 | 546.7 | 571.5 | 24.8 | 31.2 | 80 |
| CG102 | 0 | 537.6 | 531.2 | −6.4 | 0 | 0 |

The chewing gums CG 99 and CG 100 were made from the below gum bases GB 99 and GB 100 and the applied tobacco powder was added to the chewing gum composition.

|  | GB99 | GB100 |
|---|---|---|
| Elastomer | 14 | 20 |
| Resins | 40 | 37 |
| Filler | 21 | 19 |
| Plasticizers | 24.9 | 23.95 |
| Antioxidant | 0.1 | 0.05 |

The chewing gum compositions were:

|  | CG99 | CG100 |
|---|---|---|
| GB99 | 40 |  |
| GB100 |  | 42 |
| Tobacco particles | 12.7 | 6.1 |
| Bulk Sweetener | 38 | 46 |
| Flavour | 2.5 | 2.35 |
| Intense sweeteners | 1.8 | 1.25 |
| Buffer and softener | 5.0 | 2.3 |

Table 9 shows that about 35% of tobacco fibers are released in an extruded chewing gum pellet (CG 99), It should be noted that the retention of tobacco particles refer to the fibre content as initial content of e.g. humidity or other compounds, in particular hydrophilic compounds in the tobacco powder will at least to some extend be released during chewing. In the present context, measurements have shown that the applied tobacco particles contains about 60% hydrophilic components and about 40% fibres.

It should also be noted that CG100 shows a relatively high release of tobacco fibers. In this context, it should be noted that compressed chewing gum release nicotine even faster than CG99 which is a conventional mixed chewing gum. Hence, the relative release of fibres is also less than the release of nicotine in CG100.

It has been shown that fibres of tobacco particles showed retention in the gum base and only moderate transferring of the tobacco fibre content of the tobacco particles into the saliva occurs when using a mixed chewing gum even in spite of the fact that the nicotine releases faster.

Other visual tests performed on extruded or batch mixed chewing gums indicated that fibre content of the tobacco powder is retained to a large degree in spite of the fact that the chewing gum tested all showed increased release of nicotine compared to conventional nicotine chewing gum, where the nicotine is contained in e.g. NPR. In other words, there were clear indications that the chewing gums according to the provisions of the invention were able to retain substantial amounts of the tobacco fibres and release the nicotine contained in the tobacco powder.

Example 10

Preparation of Gum Base with Tobacco Particles

The composition of a further gum base is presented in Table 10.

TABLE 10

Gum base composition. Amounts are given in wt-% of the gum base.

|  | GB std. |
|---|---|
| Elastomer | 16.0 |
| Resins | 44.5 |
| Filler | 5.0 |
| Tobacco particles | 10.0 |
| Plasticizers | 24.4 |
| Antioxidant | 0.1 |

GB = Gum Base.

As compared to the gum base of example 1, tobacco particles are included in the gum base. This gum base is further made into a chewing gum as described in example 2, only without the tobacco particles. However, obviously a combination of tobacco particles inside and outside a gum base may be used as well within the scope of the present invention.

What is claimed is:

1. A chewing gum formulation comprising tobacco particles and a gum base, wherein the gum base comprises one or more hydrophobic gum base polymers, and wherein the tobacco particles are made from tobacco leaves,
    wherein the amount of tobacco particles is between 0.5 and 30% by weight of the chewing gum formulation,
    wherein nicotine is released from the tobacco particles when chewing the chewing gum formulation,
    wherein at least 50% by weight of the tobacco particles have a size above 300 μm, and
    wherein at least 30% of tobacco fibres comprised in the tobacco particles are retained in the chewing gum after the chewing gum has been chewed in vitro in accordance with European Pharmacopeia 4th. ed. 2.9.25 in a pH 7.4 phosphate buffer for 10 minutes.

2. The chewing gum formulation of claim 1, wherein at least 75% by weight of the tobacco particles have a size above 300 μm.

3. The chewing gum formulation of claim 1 wherein at least 40% of the tobacco fibres comprised in the tobacco particles are retained in the chewing gum after the chewing gum has been chewed in vitro in accordance with European Pharmacopeia 4th. ed. 2.9.25 in a pH 7.4 phosphate buffer for 10 minutes.

4. The chewing gum formulation of claim 3 wherein at least 50% of the tobacco fibres comprised in the tobacco particles are retained in the chewing gum after the chewing gum has been chewed in vitro in accordance with European Pharmacopeia 4th. ed. 2.9.25 in a pH 7.4 phosphate buffer for 10 minutes.

5. The chewing gum formulation of claim 1 wherein more than 40% of a total nicotine content in the chewing gum formulation is released from the chewing gum formulation within the first 10 minutes from initiation of a chewing process carried out in vitro on a chewing machine in accordance with European Pharmacopeia 4 th. ed. 2.9.25, with a phosphate buffer with a pH of 7.4.

6. The chewing gum formulation of claim 5 wherein more than 55% of the total nicotine content in the chewing gum formulation is released from the chewing gum formulation within the first 10 minutes from initiation of a chewing process carried out in vitro on a chewing machine in accordance with European Pharmacopeia 4 th. ed. 2.9.25, with a phosphate buffer with a pH of 7.4.

7. The chewing gum formulation of claim 6 wherein more than 75% of the total nicotine content in the chewing gum formulation is released from the chewing gum formulation within the first 10 minutes from initiation of a chewing process carried out in vitro on a chewing machine in accordance with European Pharmacopeia 4 th. ed. 2.9.25, with a phosphate buffer with a pH of 7.4.

8. The chewing gum formulation of claim 1 wherein the chewing gum formulation comprises buffer in an amount of 0.1% to 10% by weight of the chewing gum.

9. The chewing gum formulation of claim 8 wherein the chewing gum formulation comprises buffer in an amount of 0.5% to 5% by weight of the chewing gum.

10. The chewing gum formulation of claim 8 wherein the buffer is selected from the group consisting of sodium carbonate, sodium hydrogen carbonate, potassium carbonate, potassium hydrogen carbonate, dipotassium phosphate, potassium citrate, and any combination thereof.

11. A chewing gum formulation comprising tobacco particles and a gum base, wherein the gum base comprises one or more hydrophobic gum base polymers, and wherein the tobacco particles are made from tobacco leaves,
wherein the amount of tobacco particles is between 0.5 and 30% by weight of the chewing gum formulation,
wherein nicotine is released from the tobacco particles when chewing the chewing gum formulation,
wherein at least 50% by weight of the tobacco particles have a size between 50 and 2000 µm, and
wherein at least 40% of tobacco fibres comprised in the tobacco particles are retained in the chewing gum after the chewing gum has been chewed in vitro in accordance with European Pharmacopeia 4th. ed. 2.9.25 in a pH 7.4 phosphate buffer for 10 minutes.

12. The chewing gum formulation of claim 11 wherein at least 75% by weight of the tobacco particles have a size between 50 and 2000 µm.

13. The chewing gum formulation of claim 11 wherein at least 50% by weight of the tobacco particles have a size between 50 and 1200 µm.

14. The chewing gum formulation of claim 13 wherein at least 50% by weight of the tobacco particles have a size between 50 and 750 µm.

15. The chewing gum formulation of claim 13 wherein at least 50% by weight of the tobacco particles have a size between 100 and 1200 µm.

16. The chewing gum formulation of claim 13 wherein at least 50% by weight of the tobacco particles have a size between 300 and 750 µm.

17. The chewing gum formulation of claim 11 wherein at least 50% of the tobacco fibres comprised in the tobacco particles are retained in the chewing gum after the chewing gum has been chewed in vitro in accordance with European Pharmacopeia 4th. ed. 2.9.25 in a pH 7.4 phosphate buffer for 10 minutes.

18. The chewing gum formulation of claim 11 wherein more than 40% of a total nicotine content in the chewing gum formulation is released from the chewing gum formulation within the first 10 minutes from initiation of a chewing process carried out in vitro on a chewing machine in accordance with European Pharmacopeia 4 th. ed. 2.9.25, with a phosphate buffer with a pH of 7.4.

19. The chewing gum formulation of claim 18 wherein more than 55% of the total nicotine content in the chewing gum formulation is released from the chewing gum formulation within the first 10 minutes from initiation of a chewing process carried out in vitro on a chewing machine in accordance with European Pharmacopeia 4 th. ed. 2.9.25, with a phosphate buffer with a pH of 7.4.

20. The chewing gum formulation of claim 19 wherein more than 75% of the total nicotine content in the chewing gum formulation is released from the chewing gum formulation within the first 10 minutes from initiation of a chewing process carried out in vitro on a chewing machine in accordance with European Pharmacopeia 4 th. ed. 2.9.25, with a phosphate buffer with a pH of 7.4.

21. The chewing gum formulation of claim 11 wherein the chewing gum formulation comprises buffer in an amount of 0.1% to 10% by weight of the chewing gum.

22. The chewing gum formulation of claim 21 wherein the chewing gum formulation comprises buffer in an amount of 0.5% to 5% by weight of the chewing gum.

23. The chewing gum formulation of claim 21 wherein the buffer is selected from the group consisting of sodium carbonate, sodium hydrogen carbonate, potassium carbonate, potassium hydrogen carbonate, dipotassium phosphate, potassium citrate, and any combination thereof.

* * * * *